United States Patent
Hamm

(10) Patent No.: US 10,835,708 B2
(45) Date of Patent: Nov. 17, 2020

(54) LAYERED YARN AND WEIGHTED BLANKET FOR DEEP PRESSURE THERAPY

(71) Applicant: Kathrin Hamm, Nufringen (DE)

(72) Inventor: Kathrin Hamm, Nufringen (DE)

(73) Assignee: BEARABY INC., Brooklyn, NY (US)

(*) Notice: Subject to any disclaimer, the term of this patent is extended or adjusted under 35 U.S.C. 154(b) by 126 days.

(21) Appl. No.: 16/193,792

(22) Filed: Nov. 16, 2018

(65) Prior Publication Data

US 2020/0155791 A1    May 21, 2020

(51) Int. Cl.
| | | |
|---|---|---|
| *A61M 21/02* | (2006.01) | |
| *D04B 1/22* | (2006.01) | |
| *D04B 21/20* | (2006.01) | |
| *D04B 31/00* | (2006.01) | |
| *A61M 21/00* | (2006.01) | |

(52) U.S. Cl.
CPC .............. *A61M 21/02* (2013.01); *D04B 1/22* (2013.01); *D04B 21/20* (2013.01); *D04B 31/00* (2013.01); *A61M 2021/0022* (2013.01); *D10B 2509/00* (2013.01)

(58) Field of Classification Search
CPC ................................ A61M 21/02; A47G 9/02
USPC ........................................... 5/482, 485, 494
See application file for complete search history.

(56) References Cited

U.S. PATENT DOCUMENTS

| | | |
|---|---|---|
| 4,958,663 A | 9/1990 | Miller et al. |
| 5,198,288 A | 3/1993 | Grunfeld |
| 5,860,350 A | 1/1999 | Rexroad |
| 6,015,618 A | 1/2000 | Orima |
| 6,240,716 B1 | 6/2001 | Yanagawase et al. |
| 6,440,556 B2 | 8/2002 | Matsui et al. |
| 7,870,623 B2 | 1/2011 | Judd |

(Continued)

FOREIGN PATENT DOCUMENTS

| | | |
|---|---|---|
| DE | 19828218 A1 | 12/1999 |
| WO | 2014116163 A1 | 1/2014 |

(Continued)

OTHER PUBLICATIONS

"Giganto-Blanket Faq" (Nocturnal Knits) Oct. 17, 2011 (Oct. 17, 2011); retrieved from the internet Nov. 22, 2019; URL=https://nocturnalknits.com/giganto-blanket-faq/; entire document.

(Continued)

*Primary Examiner* — Fredrick C Conley
(74) *Attorney, Agent, or Firm* — BakerHostetler

(57) ABSTRACT

Disclosed is a weighted material that is configured to effectuate deep pressure therapy to a person when a piece of the weighted material is used as a blanket over the person's body. A length of layered yarn is interlooped to form the piece of weighted material. The layered yarn includes an outer tube extending longitudinally from a first end to a second end. The outer tube defines a conduit extending longitudinally therethrough from the first end to the second end. A plurality of inner layers of material are disposed within the conduit and extend longitudinally from the first end to the second end. The interlooped length of yarn, by itself, is configured and sufficiently weighted to effectuate deep pressure therapy to a person when the blanket lies over the person's body. Various other systems and methods are also disclosed.

23 Claims, 7 Drawing Sheets

(56) References Cited

U.S. PATENT DOCUMENTS

| | | |
|---|---|---|
| 2001/0053646 A1 | 12/2001 | Tanaka et al. |
| 2006/0135021 A1 | 6/2006 | Calhoun et al. |
| 2006/0174410 A1 | 8/2006 | Mastandrea, Jr. |
| 2011/0047698 A1 | 3/2011 | Parker |
| 2015/0366734 A1* | 12/2015 | Kjell .................... A61M 21/02 601/84 |
| 2017/0295887 A1 | 10/2017 | Torres et al. |
| 2018/0305847 A1* | 10/2018 | Wen ........................ D02G 3/34 |

FOREIGN PATENT DOCUMENTS

| | | |
|---|---|---|
| WO | 2014166556 A1 | 10/2014 |
| WO | 2018013025 A1 | 1/2018 |

OTHER PUBLICATIONS

International Search Report from PCT/US2019/055194 as prepared by the ISA/US; dated Dec. 27, 2019.
PDF of http://www.Ohhio.com (visited Oct. 29, 2018); English Translations of Foreign References.

* cited by examiner

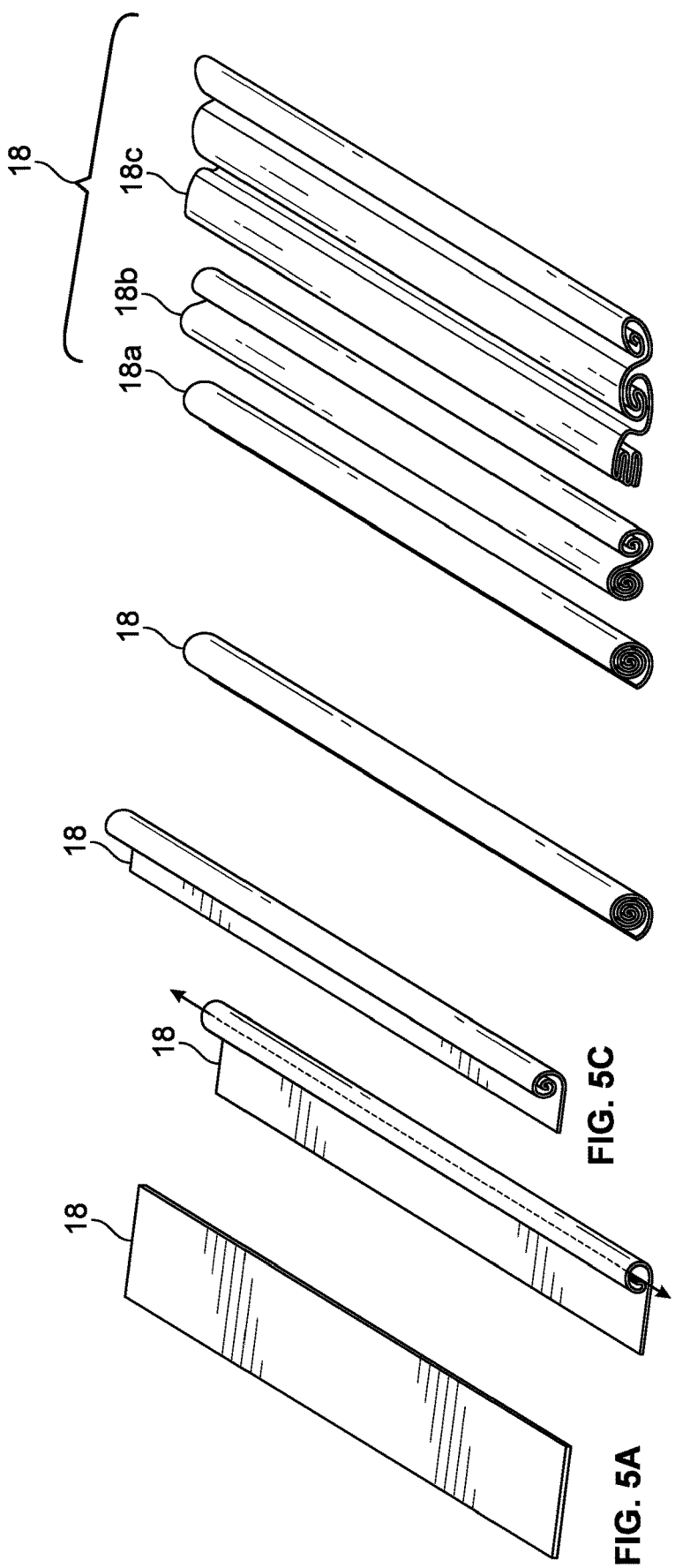

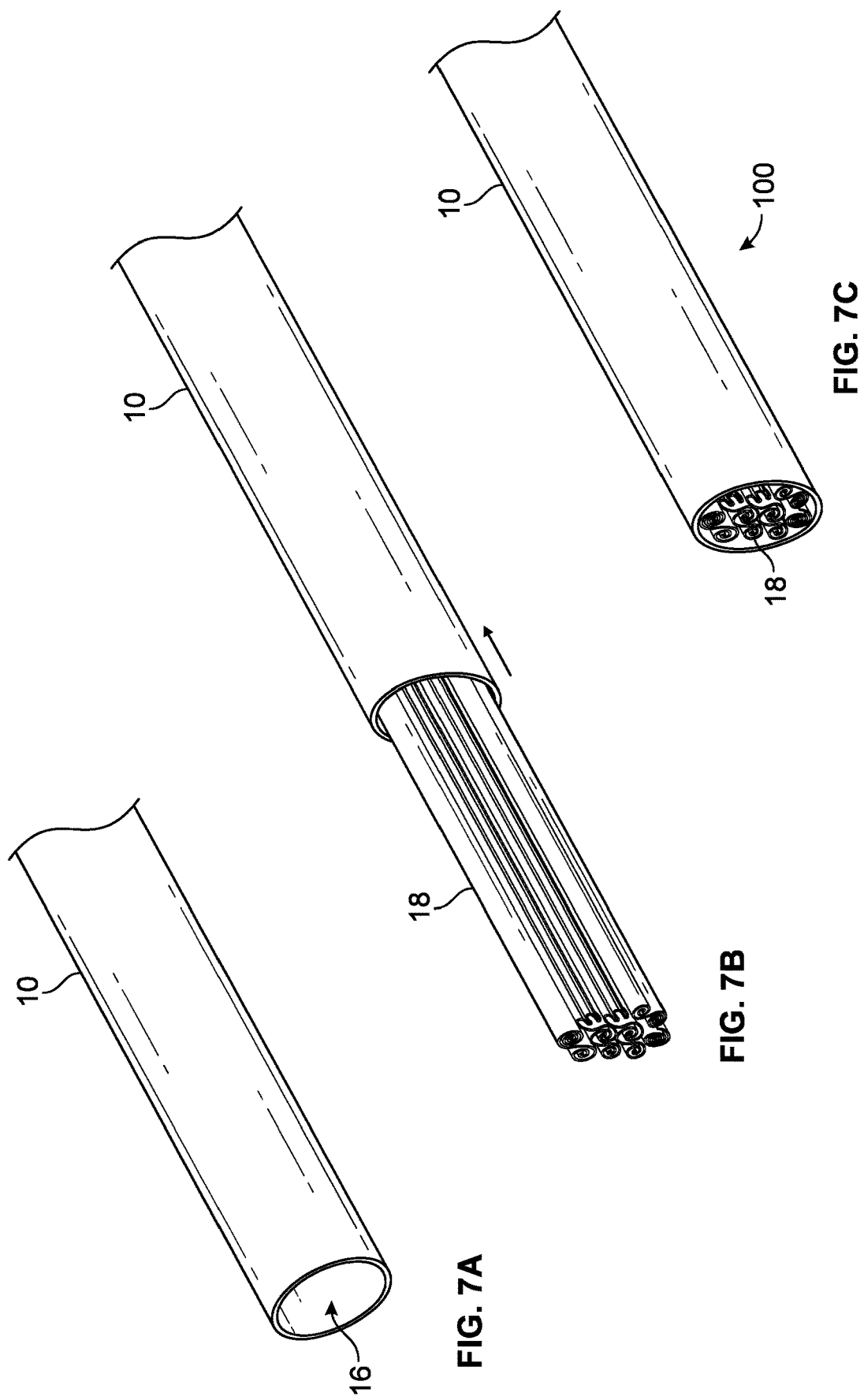

LAYERED YARN AND WEIGHTED BLANKET FOR DEEP PRESSURE THERAPY

BACKGROUND

This disclosure is directed generally to a weighted material that can be used as a weighted blanket to provide a person with deep pressure therapy. It is widely accepted in the medical community that deep pressure therapy may bring relief to those suffering from various disorders, such as insomnia, anxiety, and sensory disorders. Some techniques of deep pressure therapy involve placing across the body a blanket that has weights in it to apply pressure, stimulating a feeling of safety that is also experienced as being hugged or swaddled. In order to be effective, the blanket needs to weigh between about 10-20% of the person's body weight, leading to the blanket weighing between about 5 and 45 pounds.

Conventional deep pressure therapy blankets are typically weighted blankets that are made of a plurality of fabric layers with added weighted materials disposed between the layers. The added weighted materials typically include, for example, plastic pellets or balls, glass beads, sand, gravel, or linked chain objects. The added weighted materials are usually placed in units inside the blanket, for example, in quadratic patches that are sewn or stitched to hold the weights. In these conventional approaches, the added materials are required to provide weight because conventional fabric and multiple layers of fabric are not heavy enough to effectively provide deep pressure therapy when placed on a person.

The need for the added weights, however, carries with it several disadvantages. For example, the added weights limit breathability. The added weights and the multiple layers of fabric reduce natural airflow through the blanket. This makes it particularly difficult to regulate the body temperature of an individual when the blanket is placed on them. As another example, the added weights are prone to moving and shifting with the blanket. This substantially impairs equal, even, and continuous weight distribution, which is needed to effectuate deep pressure therapy. Also, the added weights typically cause the blanket to be overly thick and less bendable, preventing the blanket from naturally taking the body shape of a person lying under it and thereby diminishing the surface contact area of the pressure therapy.

Needed is a weighted material that can be used as a blanket to effectively produce deep pressure therapy to an individual, without the need for additional weight materials.

SUMMARY

As will be described in greater detail below, the instant disclosure describes a weighted blanket that is configured to effectuate deep pressure therapy, without the need for external weights.

In one example, a weighted material is provided. The weighted material is configured to effectuate deep pressure therapy to a person when a piece of the weighted material is used as a blanket over the person's body. A length of layered yarn is interlooped to form the piece of weighted material. The layered yarn includes an outer tube extending longitudinally from a first end to a second end. The outer tube defines a conduit extending longitudinally therethrough from the first end to the second end. A plurality of inner layers of material are disposed within the conduit and extend longitudinally from the first end to the second end. The interlooped length of yarn creates a weighted blanket that is configured and sufficiently weighted to effectuate, by itself, deep pressure therapy to a person when the blanket lies over the person's body. Various other systems and methods are also disclosed.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIGS. 5A-5E show forming inner layers by folding an inner sheet, according to an embodiment

FIGS. 7A-7C show constructing a layered yarn, according to an embodiment.

Figure 1:
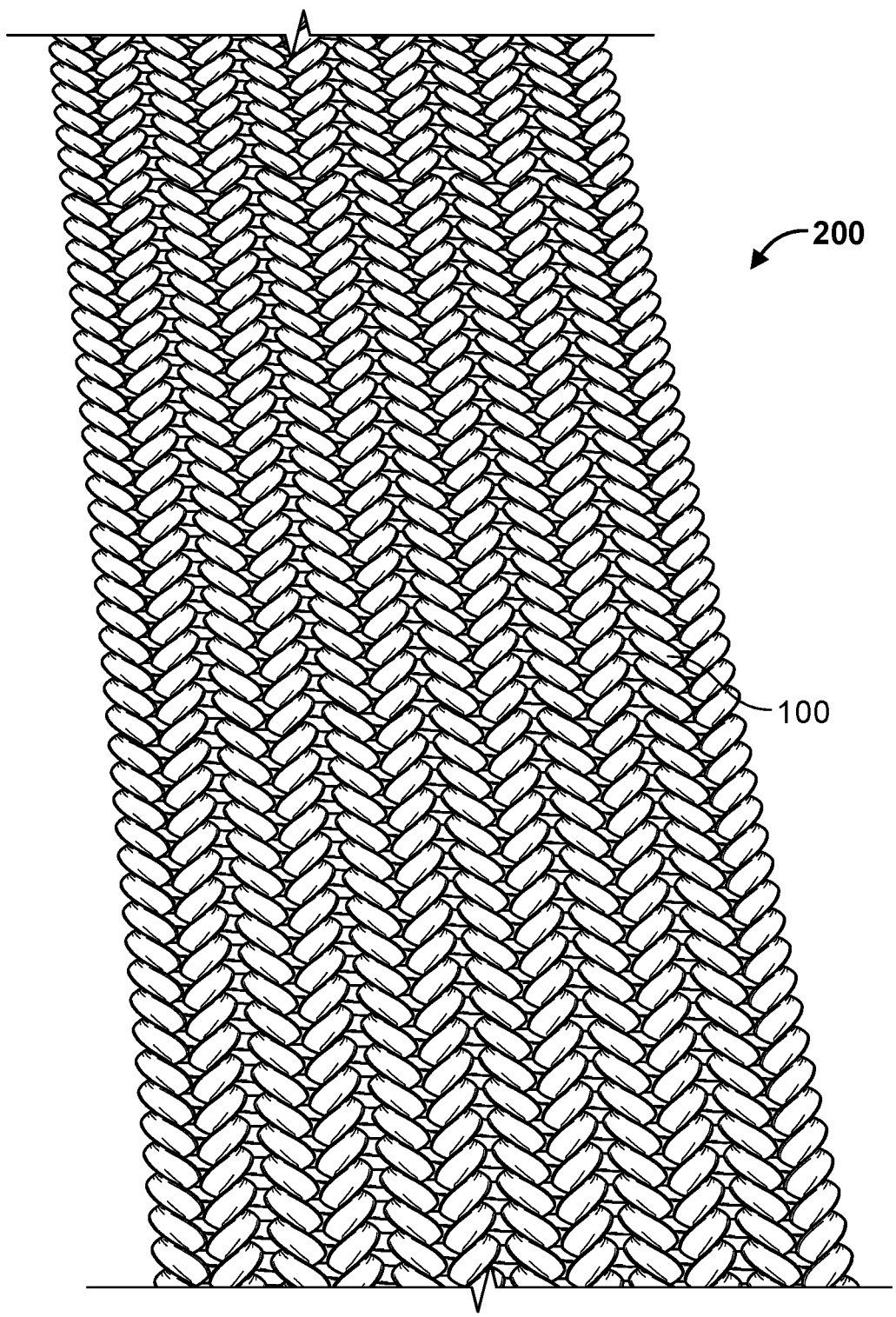
FIG. 1 is a top view of a weighted material comprising a layered yarn that is interlooped, according to an embodiment.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. The exemplary embodiments described herein, however, are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to a weighted material that can be used as a blanket to provide a person with deep pressure therapy, without the need for weights or components.

As used herein, the terms "providing deep pressure therapy," "bringing about deep pressure therapy" or "effectuating deep pressure therapy" and those similar thereto, refer to effectively causing deep pressure therapy (also known as deep pressure stimulation, deep touch pressure, etc.) in a person as herein described. More particularly, the terms "providing deep pressure therapy," "bringing about deep pressure therapy" or "effectuating deep pressure therapy" and those similar thereto, refer to physically contacting an individual to effectively cause the individual's nervous system activity to switch from being dominated by their sympathetic nervous system to being dominated by their parasympathetic nervous system.

An individual's autonomic nervous system (ANS) receives information from the individual's body and environment, and in response thereto, sends signals out to regulate the individual's body and organs. The ANS includes the sympathetic and parasympathetic systems, which work together to help the individual physiologically respond in accordance with the information the ANS receives.

The sympathetic nervous system is often referred to as the "alert" or "fight or flight" response that is elicited during stressful or emergency situations. The parasympathetic nervous system, on the other hand, is responsible for regulating involuntary functions, such as heart rate and blood pressure, and stimulating the digestive tract. It brings a sense of calm and peace to the mind and body. When the parasympathetic nervous system takes over, an individual's heart rate slows, muscles relax, and circulation improves. When deep pressure is correctly applied, it relaxes the nervous system, causing the body to switch from running its sympathetic nervous system to its parasympathetic nervous system.

Deep touch pressure may also alter the person's hormone levels by decreasing their level of cortisol (which causes and anxiety) while increasing their levels of serotonin and dopamine (which help with mood regulation and relaxation).

The disclosed systems and methods include a weighted material 200 that provides a person with tactile sensory input, which provides proprioceptive input to the individual's body. The weighted material 200 is configured such that when it is administered as a blanket to cover an individual's body, it brings about deep pressure therapy, thus causing the individual's parasympathetic system to increase and their sympathetic system to decrease.

FIG. 1 is a top view of a piece of weighted material 200 comprising a layered yarn 100 that is interlooped (e.g., knit, crocheted, etc.), according to an embodiment. The construction of the layered yarn 100, together with the interlooping thereof, provides a material 200 that is sufficiently heavy to provide deep pressure therapy (DPT) to a person without the need for additional weights. The weighted material 200 is configured so that the interlooped layered yarn 100 (e.g., one layer of the interlooped layered yarn 100), by itself and without any added weights or components, brings about deep pressure therapy in an individual, when the weighted material 200 is employed as a blanket over the individual.

As will be described in further detail below, the disclosed weighted material 200 can be employed as a deep pressure therapy blanket that provides many advantageous that are not provided by conventional deep pressure therapy blankets. For example, the disclosed weighted material 200 comprises layered yarn 100 that is interlooped in a pattern that creates small openings at the crossing of the loops. This allows for even airflow through the blanket, thus providing desirable breathability and helping to regulate the person's body temperature.

The interlooping of the layered yarn 100 creates heavy knots at the cross-sections of the loops. This pattern of heavy knots, in turn, creates a pattern of pressure regions on the individual when the weighted blanket 200 is placed over them. This provides a highly effective deep pressure therapy blanket.

Also, the disclosed weighted material 200 offers even weight distribution. The layered yarn 100 may be evenly interlooped (e.g., knit, crochet) in equally sized, enmeshed loops, which distributes the weight substantially equally across the structure of the weighted material 200. The layered yarn 100 is sufficiently heavy and is fixated through the wide-looped pattern. Thus, unlike conventional DPT blankets, the weight does not shift throughout the structure of the weighted material 200 when the weighted material 200 moves. This is highly advantageous, as continuously maintaining an even weight distribution across the individual is imperative to the efficacy of deep pressure therapy.

Also, the disclosed weighted material 200 provides improved body-contouring abilities. The stretchability of the interlooped layered yarn 100 may take a natural body contouring shape and can adapt to each individual body shape, thus creating a direct and increased surface area for the weight to apply gentle and even pressure across the body. Several other benefits and advantageous may be recognized as well.

FIG. 1 shows an embodiment of a weighted material 200 that is constructed by interlooping layered yarn 100 through a knitting technique. Additionally or alternatively, other suitable techniques of interlooping the layered yarn 100 (e.g., crocheting, looping, etc.) may be implemented to form the weighted material 200 while remaining within the scope of this invention. For example, FIG. 9B show a piece of weighted material 200 that is constructed by interlooping the layered yarn 100 through a crocheting technique.

The piece of weighted material 200 shown in FIG. 1 can be utilized as a blanket, for example, for covering a large percentage (e.g., a majority) of a person's body when the person is lying down. In some embodiments, a blanket comprising only a single layer of the weighted material 200 provides sufficient weight to effectuate deep pressure therapy on the person. For example, the weighted material 200 may have a length, width, and height; and the layered yarn 100 may have a longitudinal length and a diameter perpendicular thereto. The height of the weighted material 200 may be equal to the diameter of the layered yarn 100. In other words, the weighted material 200 may consist of only a single layer of the interlooped layered yarn 100 that is sufficiently weighted to effectuate deep pressure therapy when placed over the person's body.

Figure 2:
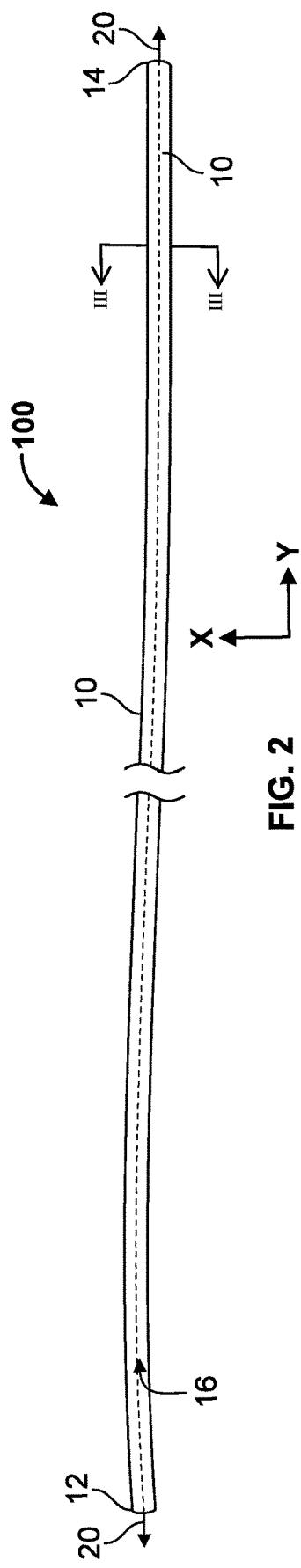
FIG. 2 is a side view of a layered yarn that can be interlooped to construct the weighted material of FIG. 1, according to an embodiment.
Figure 4:
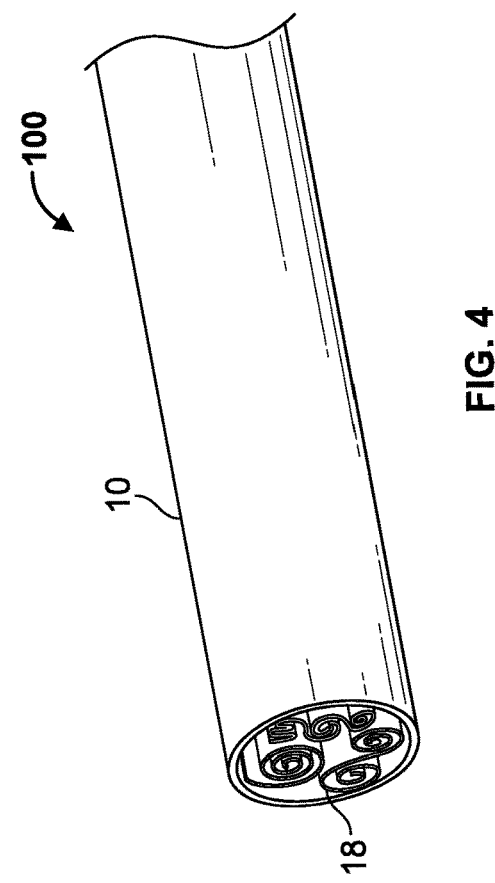
FIG. 4 is a perspective view of the layered yarn of FIG. 2, according to an embodiment.
Figure 3:
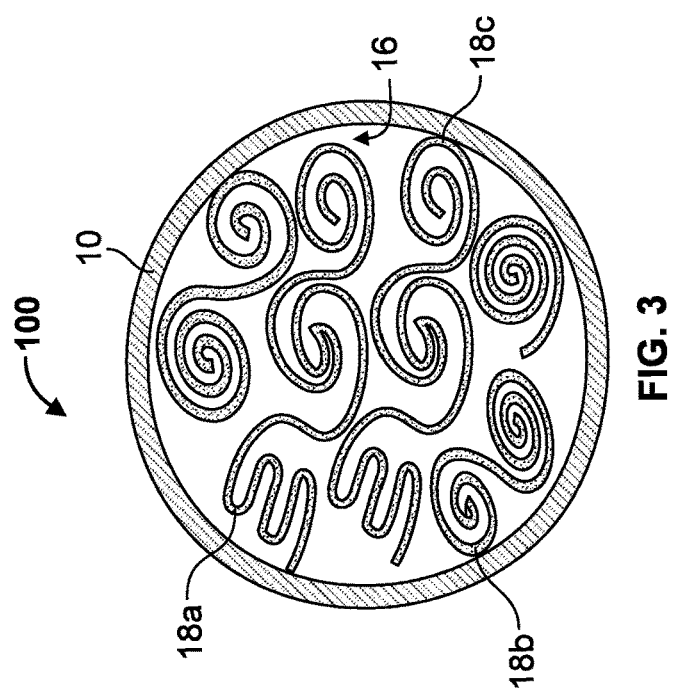
FIG. 3 is a cross-sectional view of the layered yarn of FIG. 2 taken across line III-III, according to an embodiment.

FIGS. 2-4 are side, cross-sectional, and perspective views of a length of layered yarn 100, according to an embodiment. The term yarn, as used herein, refers to a continuous strand of material that can be manipulated (e.g., interlooped) to form a fabric. The layered yarn 100 may be interlooped to provide a piece of weighted material, for example, the piece of weighted material 200 shown in FIG. 1. The layered yarn 100 comprises an outer tube 10 and a plurality of inner layers 12. The outer tube 10 and the inner layers 12 are made from textile material, further details of which are provided below with reference to FIGS. 3 and 4. The outer tube 10 extends longitudinally from a first end 12 to a second end 14. While FIG. 2 shows an embodiment in which the first end 12 and second end 14 are separated from one another, in other embodiments, the length of yarn 100 may comprise a loop, in which the first end 12 and the second end 14 are connected to each other.

The outer tube 10 defines a conduit 16 that extends longitudinally therethrough, from the first end 12 to the second end 14. A plurality of inner layers 18 of material are disposed within the conduit 16 and extend longitudinally from the first end 12 to the second end 14.

The inner layers 18 may be formed by folding at least one inner sheet 18 about at least one fold axis extending substantially longitudinally from the first end 12 to the second end 14. The inner layers 18 may be configured to provide equal weight distribution along the longitudinal length of the layered yarn 100. The inner sheets 18 may be folded longitudinally in any suitable configuration. One or more of the inner sheets 18 may be folded about its respective fold axis a plurality of rotations to provide a coil shape. In some embodiments, the inner sheet is folded about a plurality of fold axes, each of plurality of fold axes extending longitudinally. The inner layers 18 may comprise any suitable number of folded inner sheets 18, such as one to twenty folded inner sheets 18, for example, one to four folded inner sheets 18.

As shown in FIGS. 3 and 4, the inner sheet 18 is folded onto itself into one or more coiled or otherwise folded configuration. As shown in FIGS. 3 and 4, the plurality of inner sheets 18 can each be folded in various fold arrangements. For example, FIG. 3 shows inner sheet 18a that is folded about one respective fold axis in a plurality of rotations to provide a coil shape. FIG. 3 also shows inner sheet 18b that is folded about two respective fold axes in a plurality of rotations to provide two coil shapes. The fold arrangements shown and described herein are exemplary, and the inner layers 18 may comprise any suitable fold arrangement while remaining within the scope of this disclosure.

The fold axis may extend substantially longitudinally from the first end 12 to the second end 14, so that the inner sheet is folded onto itself lengthwise. The fold axis, however, does not need to be entirely straight or parallel to the longitudinal axis of the layered yarn 100. For example, the folded inner sheet 18 may be twisted or squished along the length of the layered yarn 100.

The plurality of inner layers 18 may extend uninterrupted along the longitudinal length of the layered yarn 10. For example, the at least one folded inner sheets 18 may be uninterrupted along the longitudinal length (e.g., extending uninterrupted from the first end 12 to the second end 14 of the layered yarn 100). This may provide a layered yarn 100 having a substantially homogeneous weight distribution along its length, which in turn may provide a weighted material 200 that has a substantially homogeneous weight distribution across its surface.

The plurality of inner layers 18 may be disposed within the conduit 16 and fill the conduit 16 of the hollow tube 10 by any suitable proportion. For example, the folded inner sheets 18 may take up between about 75-99% of the volume of the conduit 16. For example, the folded inner sheets 18 may take up between about 85-95% of the volume of the conduit 16. For example, the folded inner sheets may take up between about 90% of the volume of the conduit 16. The inner layers 18 may be configured to take up enough volume within the conduit to provide sufficient weight, while allowing for sufficient air flow to flow through the layered yarn 100.

The outer tube 10 and inner layers 18 may be made of any suitable textile materials, for example, spun and/or woven fibers. The outer tube 10 and/or inner layers 18 may be made out of cotton, for example, organic cotton (e.g., entirely made of 100% organic cotton). The outer tube 10 and/or inner layers 18 may include a material that demonstrates high stretching properties, such as elastane, to facilitate interlooping the yarn 100.

In some embodiments, the outer tube 10 is made of a cotton-elastane mix, and the inner layers 18 are made almost entirely (e.g., entirely) of cotton (e.g., entirely made of 100% organic cotton). This construction provides a layered yarn 100 that demonstrates sufficient stretchability (from the elastane material in the outer tube) to facilitate interlooping of the layered yarn 100 and body contouring of the weighted material 200, while also maintaining sufficient rigidity (from the cotton in the outer tube, and the cotton inner layers) to provide steady weight distribution of the blanket 200.

The weighted material 200 may have any suitable dimensions to be employed as a blanket over a person laying down to bring about deep pressure therapy. For example, the weighted material 200 may be have a length between 50 and 80 inches, for example, between 65 and 75 inches. The weighted material 200 may have a width between about 35 and 70 inches, for example, between 45 and 55 inches. In some embodiments, a piece of material 200 is about 48 inches wide, 72 inches long, and 2 inches high, and is made of a length of interlooped layered yarn 100 that is about 250 meters long and that has a diameter of about 2 inches.

The weighted material 200 may be configured to weigh between 5 lb and 45 lb for example, between 7 lb and 40 lb, for example, between 10 and 35 lb. The weighted material 200 may weigh between about 10% and 20% of a person's body weight, and the weighted material 200 may be configured to bring about deep pressure therapy for a person weighing between, for example, 35 lb and 400 lb. In some embodiments, the piece of weighted material 200 has dimensions of about 48×72×2 inches, weighs between 20 and 35 lb, and is constructed from a length of interlooped layer yarn that is about 250 meters long and has a diameter of about 2 inches.

The layered yarn 100 may have a diameter between about 1 and 5 inches. For example, the layered yarn 100 may have a diameter between about 1.5 and 3 inches. In some embodiments, the layered yarn 100 has a diameter of about 2 inches. In some embodiments, the plurality of inner layers 18 comprise folded inner sheets 18 that have a length that is substantially the same as the length of the hollow tube 10, and the inner sheets 18 have a width that is greater than the diameter of the hollow tube 10.

FIGS. 5A-5E show a schematic representation of forming inner layers 18 by folding an inner sheet 18, according to an embodiment. FIG. 5A shows an inner sheet 18 that is in a substantially flat configuration. The inner sheet 18 shown in FIG. 5A may be formed of a larger sheet 18 that is folded along one or more fold lines to provide the substantially flat configuration shown in FIG. 5A. FIGS. 5B and 5C show the inner sheet 18 of FIG. 5A as it is being rolled along the longitudinally extending fold axis 22. FIG. 5D shows the inner sheet 18 of FIGS. 5A-5C that is rolled along the longitudinally extending fold axis 22. FIG. 5E shows the inner sheet 18a of FIGS. 5A-5D, together with additional inner sheets 18b, 18c that are each folded along their respective longitudinally extending fold axes. The inner sheets 18 can be arranged within the hollow tube 10 to form the layered yarn 100.

Figure 6A:
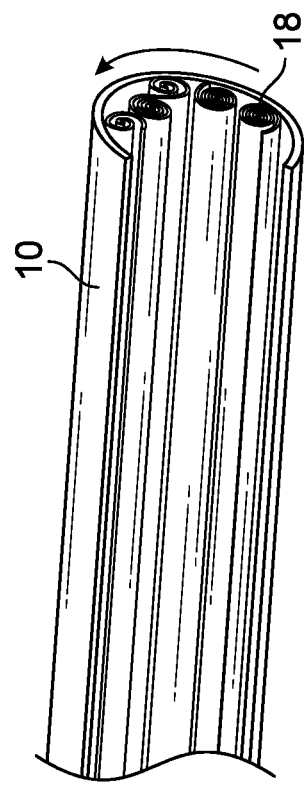
FIGS. 6A-6C show constructing a layered yarn, according to an embodiment.
Figure 6B:
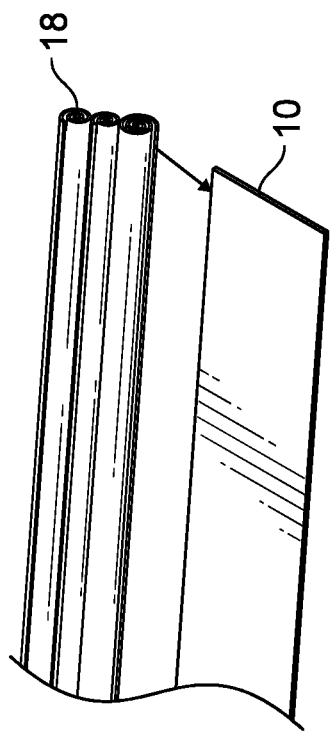
Figure 6C:
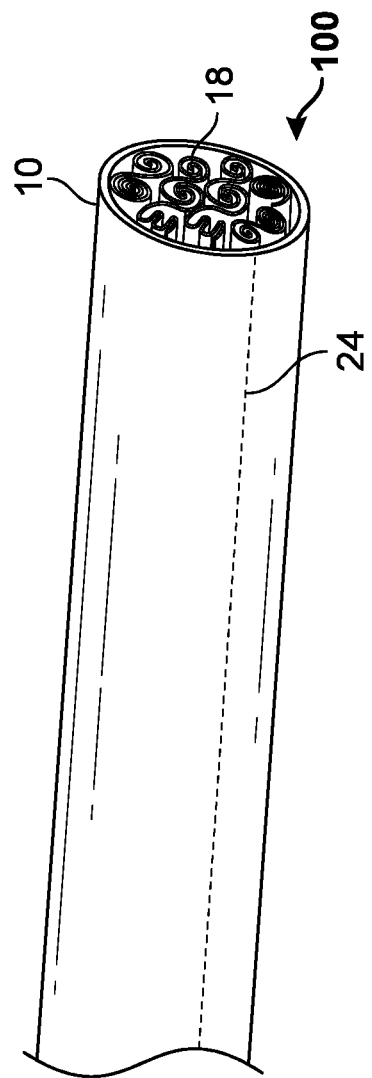

FIGS. 6A-6C show a schematic representation of constructing a layered yarn 100, according to an embodiment. FIG. 6A shows the outer layer 10 that is arranged as a sheet (e.g., sheet of fabric) before it is rolled into the hollow tube 10. Also shown in FIG. 6A is the at least one folded inner layer 18 as it is being arranged on top of the outer sheet 10. FIG. 6B shows the at least one folded inner layer 18 disposed on the outer sheet 10, and the outer sheet 10 being rolled into the hollow tube 10. FIG. 6C shows the hollow tube 10 rolled around the plurality of inner layers 18 to form the layered yarn 100. The outer layer 10 may be attached at seam 24 by any suitable means (e.g., stitching, adhesion, friction, hook-and-loop, etc.) to secure the hollow tube 10. The hollow tube 10 may be attached to itself at ends 12, 14 to close the conduit 16.

FIGS. 7A-7C show a schematic representation of constructing a layered yarn 100, according to an embodiment. FIG. 7A shows the outer tube 10 that is hollow, with conduit 16 extending longitudinally therethrough. In some embodiments, the outer tube 10 is formed by rolling an outer layer sheet 10 and securing it at a seam into a tube shape (e.g., by attaching the rolled sheet by suitable means (e.g., stitching, adhesion, friction, hook-and-loop, etc.) similarly to the attachment seam 24 shown in FIG. 6C. In some embodiments, the outer tube 10 is formed as a seamless tubular structure. For example, the outer tube 10 may be formed by interlocking fibers to form the tubular configuration. FIG. 7B shows the plurality of inner layers 18 being inserted into the conduit 16 of the hollow tube 10. FIG. 7C shows the plurality of inner layers 18 that are arranged inside the hollow tube 10 to provide the layered yarn 100. The hollow tube 10 may be attached to itself at ends 12, 14 to close the conduit 16.

In some embodiments, the plurality of inner layers 18 may be attached together by any suitable means to maintain, for example, the folded configuration. For example, the at least one folded inner sheets 18 may be stitched and/or adhered to itself. Additionally or alternatively, the plurality of inner layers 18 may be attached to at least a portion of the inner tubular wall of the hollow tube 10 by any suitable means. For example, the at least one folded inner sheet 18 may be attached to the inner tubular wall of the hollow tube 10 by way of stitching, adhesion (e.g., glue), friction, hook-and-loop, etc.

Figure 8A:
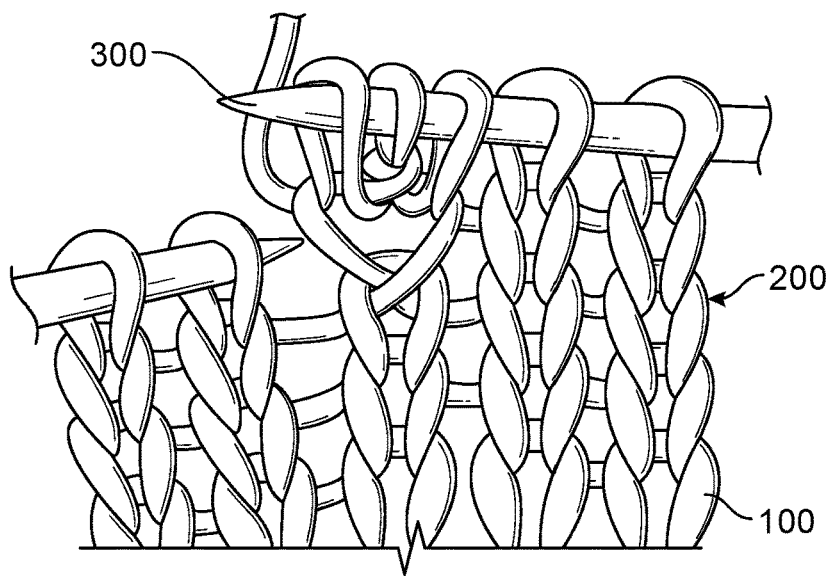
FIG. 8A is a perspective view of layered yarn being knit to construct a piece of weighted material, according to an embodiment.
Figure 9:
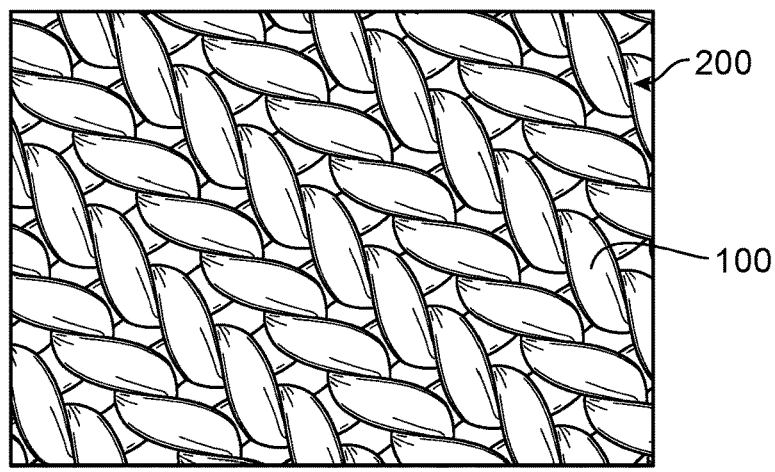
FIG. 9 is a top view of a piece of weighted material that is constructed by knitting layered yarn, according to an embodiment.

FIG. 8A is a perspective view of a layered yarn 100 that is being knit to construct a piece of weighted material 200, according to an embodiment. FIG. 9 is a top view of a piece of weighted material 200 that is constructed by knitting layered yarn 100 (e.g., as shown in FIG. 8A), according to an embodiment. The layered yarn 100 may be knit using a pair of knitting needles 300. The knitting may be performed manually by a user and/or using an automated machine. The knitting may comprise intermeshing loops of the layered yarn 100 in a number of consecutive rows. As each row progresses, a newly generated loop is pulled through one or more loops from the prior row, creating a dense pattern.

Figure 8B:
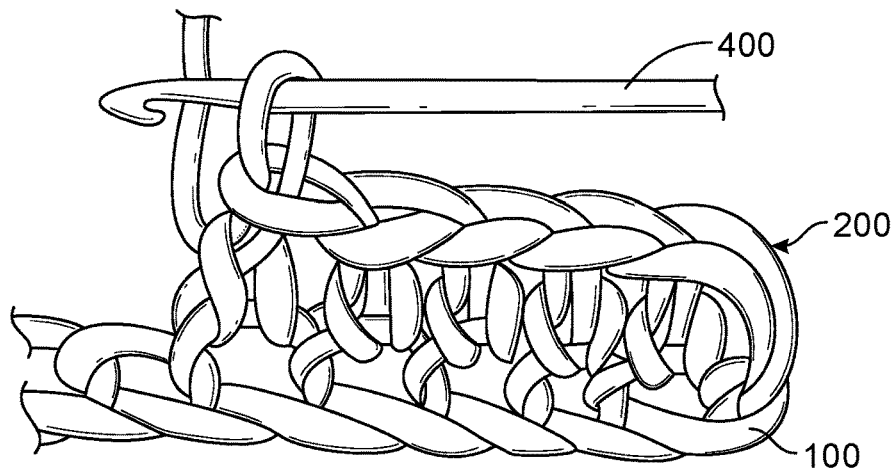
FIG. 8B is a perspective view of a layered yarn being crocheted to construct a piece of weighted material, according to an embodiment.

FIG. 8B is a perspective view of a strand of layer yarn 100 being crocheted to construct a piece of weighted material 200, according to an embodiment. The layered yarn 100 may be crocheted using a pair of crocheting needles 400, as shown. The crocheting may be performed manually by a user and/or using an automated machine. The crocheting may comprise intermeshing loops of the layered yarn 100 in a number of consecutive rows.

As shown in FIGS. 7A and 7B, the weighted material 200 comprises layered yarn 100 that is interlooped in a pattern that creates small openings at the crossing of the loops. This allows for even airflow through the blanket, thus providing desirable breathability and helping to regulate the individual's body temperature. The interlooping of the layered yarn 100 (e.g., knitting as shown in FIG. 8A, crocheting as shown in FIG. 8B), together with the construction of the layered yarn 100, creates a piece of weighted material 200 that is dense enough to provide deep pressure therapy for a person. For example, the piece of weighted material 200 can have dimensions, of about 48×72×2 inches and can weigh between 20 and 35 lb. The interlooped material 200 is both sufficiently wide-looped and dense to effectuate deep pressure therapy, while also providing superior breathability, even and continuous weight distribution, and natural body contouring capabilities.

The interlooping of the layered yarn 100 creates heavy knots at the cross-sections of the loops. This pattern of heavy knots, in turn, creates a pattern of pressure regions on the individual when the weighted blanket 200 is placed over them. This provides a highly effective deep pressure therapy blanket.

FIGS. 8A and 8B show formation of a single layer of interlooped layered yarn 100. For example, the thickness of the weighted material 200 is equal to the diameter of the layered yarn 100. In some embodiments, the layered yarn 100 is sufficiently heavy, and the layered yarn 100 is interlooped such that only a single layer of the interlooped yarn 100 creates a piece of weighted material 200 that, when employed as a blanket over a person, brings about deep pressure therapy to the person.

Figure 10:
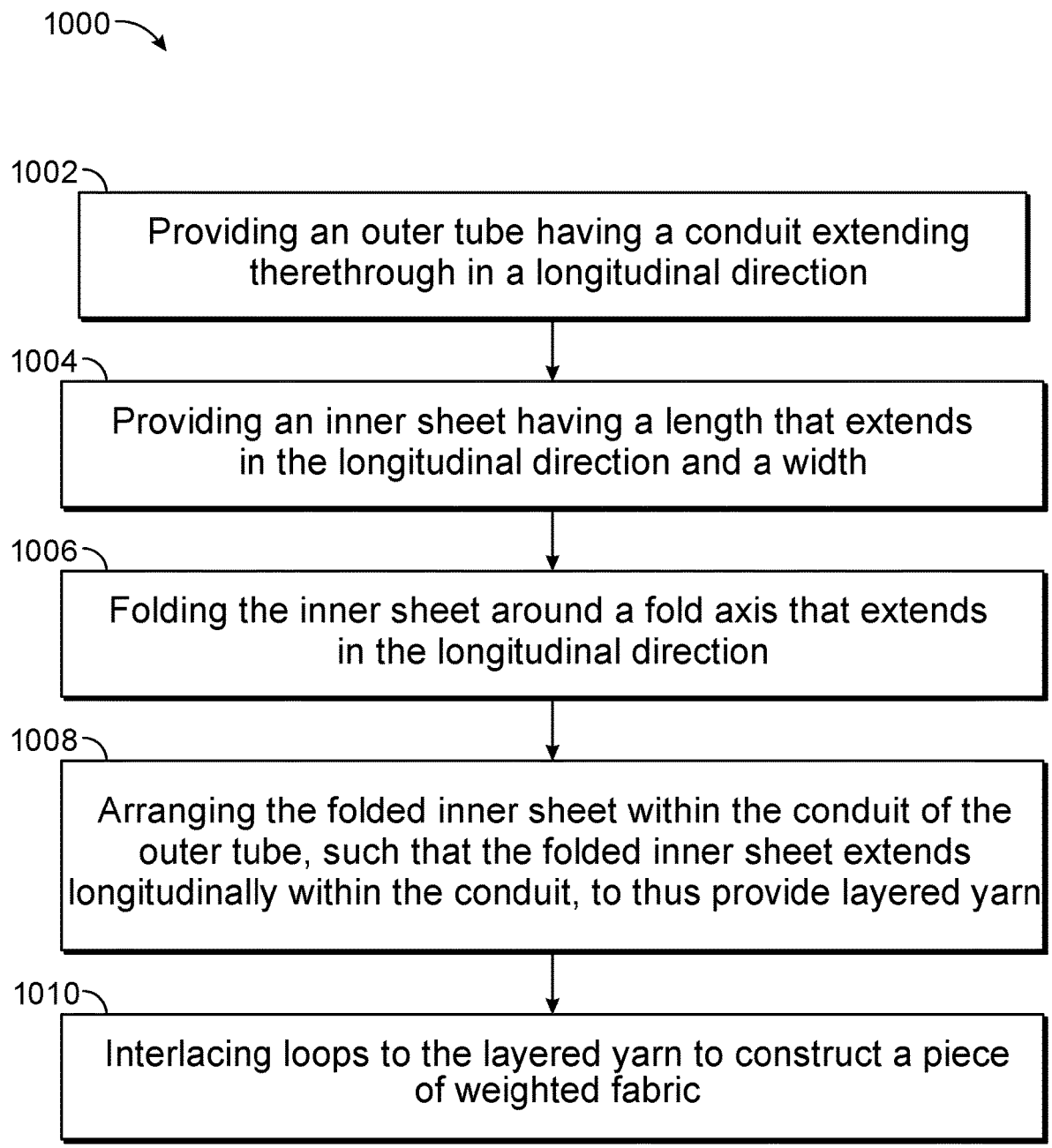
FIG. 10 is a flowchart of an exemplary method of constructing a piece of weighted material, according to an embodiment.

FIG. 10 is a flowchart of a method 1000 of constructing a piece of weighted material, according to an embodiment. In steps 1002-1008, a layered yarn is constructed. At step 1002, an outer tube is provided. The outer tube includes a conduit extending therethrough in a longitudinal direction. At steps 1004 and 1006, an inner sheet is provided and folded around a fold axis, which extends in a longitudinal direction. At step 1008, the folded inner sheet is arranged within the conduit, such that the folded inner sheet extends longitudinally within the conduit. At step 1010, the constructed layered yarn is interlooped to construct a piece of deep pressure therapy material.

The weighted material 200 of FIG. 1 is employed as a blanket over a person's body (e.g., a majority of the person's body). The piece of weighted blanket 200 may be configured to provide sufficient air circulation through the weighted blanket 200 to regulate the body temperature of the person. For example, the weighted blanket 200 may be configured to provide 18-26% air flow therethrough (e.g., from the air above the blanket 200 to the person laying beneath the weighted blanket 200).

The weighted material's 200 beneficial air flow qualities may be provided by the interlooping of the layered yarn 100 (allowing air to circulate around the layered yarn 100) as well as the construction of the layered yarn 100 (allowing air to circulate through the layered yarn 100). For example, as described above with reference to FIGS. 9A and 9B, the weighted material 200 may be created by an interlooped pattern that creates small openings at the crossing of the loops, and between the loops of layered yarn 100. Thus, air flow may travel from the top and to the bottom of the weighted material 200 through the small openings (the air flowing around the layered yarn 100). Also, the layered yarn 100 may be configured to allow air to circulate through the yarn itself. For example, the configuration of the hollow tube 10 and the plurality of layers 18 provide empty spaces within the conduit 16. Air is thus allowed to circulate along the empty spaces and through the conduit 16 (the air flowing through the layered yarn 100). In addition to providing superior air circulation, the construction of the material 200 also provides well-balanced moisture and heat transfer capabilities.

The layered yarn 100 may be configured to have a substantially homogenous weight and density along its longitudinal length. This provides many advantages over strands of material that comprise bunched up filler material. For example, the bunched up filler material creates inconsistent weight distribution, which greatly impairs even weight distribution of the weighted blanket. The layered yarn 100, however, is configured to maintain weight distribution through the interlooping of the yarn 100 and the movement and use of the blanket 200.

While the outer tube 10 and inner layers 18 are shown and described as being separate components, in some embodiments, the outer tube 10 and at least one of the inner layers 18 are integrally formed. In some embodiments, the inner layers 18 are attached (e.g., at a seam along the longitudinal length of the layered yarn 100), so the outer periphery of the attached inner layers 18 forms the outer construction of the yarn (e.g., without a separate outer tube 10).

While this disclosure describes using the piece of weighted material 200 to provide deep pressure therapy, it should be well understood that the weighted material 200 may be used for other purposes, in addition to or as an alternate to deep pressure therapy. Also, while the disclosure describes employing the piece of weighted material 200 as a blanket to lay over an individual, it should be well understood that the weighted material 200 may be employed in other suitable ways. Further, while this disclosure describes laying the piece of material 200 over a person, it should be well understood that the material 200 may be laid over other suitable kinds of animals to provide them with deep pressure therapy.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A deep pressure therapy blanket, comprising a piece of weighted material, the piece of weighted material comprising:
a length of layered yarn having loops that are interlooped to form the piece of weighted material, wherein the length of layered yarn comprises:
an outer tube extending longitudinally from a first end to a second end, the outer tube defining a conduit extending longitudinally therethrough from the first end to the second end, and the outer tube forming the loops that are interlooped; and
a plurality of inner layers of material disposed within the conduit of the outer tube and extending longitudinally from the first end to the second end,
wherein the length of layered yarn, by itself, is configured and sufficiently weighted to effectuate deep pressure therapy to a person when the deep pressure therapy blanket lies over a person's body.

2. The deep pressure therapy blanket of claim 1, wherein:
the outer tube has a diameter extending perpendicular to a longitudinal direction and the outer tube is arranged in the deep pressure therapy blanket to apply a direct pressure over the person's body;
the deep pressure therapy blanket has a length, a width, and a height; and
the height of the deep pressure therapy blanket is equal to the diameter of the outer tube.

3. The deep pressure therapy blanket of claim 1,
wherein the outer tube comprises a single layer to form the piece of weighted material,
wherein the plurality of inner layers comprise a folded inner sheet, and
wherein the folded inner sheet is folded about a fold axis that extends longitudinally from the first end to the second end.

4. The deep pressure therapy blanket of claim 3, wherein the folded inner sheet is folded about a plurality of fold axes, each extending longitudinally from the first end to the second end.

5. The deep pressure therapy blanket of claim 3, wherein the folded inner sheet is folded about the fold axis a plurality of times to provide a coil shape.

6. The deep pressure therapy blanket of claim 3, comprising a plurality of inner sheets, each of the plurality of inner sheets being folded about a respective fold axis extending substantially longitudinally from the first end to the second end.

7. The deep pressure therapy blanket of claim 1,
wherein the outer tube comprises a continuous strand of material interlooped to form the piece of weighted material, and
wherein each inner layer of the plurality of inner layers extend uninterrupted along a longitudinal length, from the first end to the second end.

8. The deep pressure therapy blanket of claim 1,
wherein the length of layered yarn is interlooped with at least one of the following: a knitting construction or a crocheting construction; and
wherein the outer tube has a diameter of 1 inch to 5 inches.

9. The deep pressure therapy blanket of claim 1, configured to allow between 18-26% air flow through the deep pressure therapy blanket; and
wherein the length of layered yarn is interlooped in a pattern that creates openings for airflow through the deep pressure therapy blanket.

10. The deep pressure therapy blanket of claim 1,
wherein the length of layered yarn has a substantially homogenous weight along its longitudinal length;
wherein the outer tube is arranged in the deep pressure therapy blanket to apply a direct pressure over the person's body;
wherein the outer tube comprises a continuous strand of material interlooped to form the piece of weighted material; and
wherein the length of layered yarn is interlooped in a pattern that creates openings for airflow through the deep pressure therapy blanket.

11. The deep pressure therapy blanket of claim 1, wherein the plurality of inner layers comprise fibers.

12. A method of constructing a piece of weighted material for a deep pressure therapy blanket, the method comprising:
constructing a length of layered yarn by:
creating an outer tube extending longitudinally from a first end to a second end, the outer tube defining a conduit extending longitudinally therethrough from the first end to the second end;

arranging a plurality of inner layers within the conduit, each of the plurality of inner layers extending longitudinally from the first end to the second end; and interlooping the length of layered yarn with loops of the outer tube to construct the piece of weighted material, wherein the length of layered yarn, by itself, is configured and sufficiently weighted to effectuate deep pressure therapy to a person when the deep pressure therapy blanket lies over a person's body.

13. The method of claim 12, wherein:
the outer tube has a diameter extending perpendicular to a longitudinal direction and the outer tube is arranged in the deep pressure therapy blanket to apply a direct pressure over the person's body;
the piece of weighted material has a length, a width, and a height; and
the height of the deep pressure therapy blanket is equal to the diameter of the outer tube.

14. The method of claim 12,
wherein each inner layer of the plurality of inner layers extend uninterrupted along a longitudinal length, from the first end to the second end; and
wherein the outer tube comprises a single layer to form the piece of weighted material.

15. The method of claim 12,
wherein the outer tube comprises a continuous strand of material interlooped to form the piece of weighted material, and
wherein interlooping the length of layered yarn comprises at least one of the following: knitting or crocheting.

16. The method of claim 12, wherein the plurality of inner layers comprise fibers.

17. A method of constructing a piece of weighted material for a deep pressure therapy blanket, the method comprising:
constructing a length of layered yarn by:
creating an outer tube extending longitudinally from a first end to a second end, the outer tube defining a conduit extending longitudinally therethrough from the first end to the second end;
folding an inner sheet about a fold axis that extends longitudinally from the first end to the second end to create at least one of a plurality of inner layers;
arranging the plurality of inner layers within the conduit, each of the plurality of inner layers extending longitudinally from the first end to the second end; and
interlooping the length of layered yarn to construct the piece of weighted material,
wherein the length of layered yarn, by itself, is configured and sufficiently weighted to effectuate deep pressure therapy to a person when the deep pressure therapy blanket lies over a person's body.

18. The method of claim 17, comprising folding the inner sheet about a plurality of fold axes, each of the plurality of fold axes extending longitudinally from the first end to the second end.

19. The method of claim 17, comprising folding the inner sheet about the fold axis a plurality of times to provide a coil shape.

20. The method of claim 17, comprising folding a plurality of inner sheets, each of the plurality of inner sheets being folded about a respective fold axis extending substantially longitudinally from the first end to the second end.

21. The method of claim 17, comprising:
providing an outer sheet of material, the outer sheet of material comprising a top surface and a bottom surface each having a length extending in a longitudinal direction from the first end to the second end, and a width extending in a lateral direction and perpendicular to a longitudinal direction;
attaching the plurality of inner layers to the top surface of the outer sheet of material; and
wrapping the outer sheet of material around a longitudinally extending tube axis to form the outer tube, the top surface of the outer sheet of material forming an interior wall of the outer tube and a bottom surface of the outer sheet of material forming an exterior wall of the outer tube,
wherein the outer tube has a diameter of 1 inch to 5 inches.

22. A piece of weighted material, comprising:
a length of layered yarn that is interlooped to form knots at cross sections of loops to form a piece of weighted material, wherein the length of layered yarn comprises:
an outer tube extending longitudinally from a first end to a second end, the outer tube defining a conduit extending longitudinally therethrough from the first end to the second end, and the outer tube arranged to form the knots at cross sections of the loops to form the piece of weighted material; and
a plurality of inner layers of material disposed within the conduit and extending longitudinally from the first end to the second end,
wherein the outer tube is arranged in the piece of weighted material to apply a direct pressure over a person's body; and
wherein the length of layered yarn, by itself, is configured and sufficiently weighted to effectuate deep pressure therapy to a person when the piece of weighted material lies over the person's body.

23. The piece of weighted material of claim 22, wherein the plurality of inner layers comprise fibers.

* * * * *